US010555904B2

(12) United States Patent
Zimmermann et al.

(10) Patent No.: US 10,555,904 B2
(45) Date of Patent: Feb. 11, 2020

(54) POUCH-LIKE STRUCTURE WITH PARACRINE ACTIVITY AND METHOD FOR ITS PREPARATION

(71) Applicant: Georg-August-Universitaet Goettingen Stiftung Oeffentlichen Rechts, Universitaesmedizin, Goettingen (DE)

(72) Inventors: Wolfram Hubertus Zimmermann, Goettingen (DE); PohLoong Soong, Goettingen (DE)

(73) Assignee: Georg-August-Universitaet Goettingen Stiftung Oeffentlichen Rechts, Universitaesmedizin, Goettingen (DE)

( * ) Notice: Subject to any disclaimer, the term of this patent is extended or adjusted under 35 U.S.C. 154(b) by 62 days.

(21) Appl. No.: 15/712,346

(22) Filed: Sep. 22, 2017

(65) Prior Publication Data

US 2018/0015029 A1 Jan. 18, 2018

Related U.S. Application Data

(62) Division of application No. 14/471,116, filed on Aug. 28, 2014, now Pat. No. 9,801,817.

(30) Foreign Application Priority Data

Aug. 30, 2013 (EP) .................................... 13182437

(51) Int. Cl.

| | |
|---|---|
| ***A61K 48/00*** | (2006.01) |
| ***A61K 9/00*** | (2006.01) |
| ***A61F 2/24*** | (2006.01) |
| ***C12N 5/071*** | (2010.01) |
| ***A61L 31/00*** | (2006.01) |
| ***A61L 31/16*** | (2006.01) |
| ***A61K 35/28*** | (2015.01) |
| ***A61K 35/33*** | (2015.01) |
| ***A61K 35/34*** | (2015.01) |
| ***A61K 35/44*** | (2015.01) |
| ***A61K 45/06*** | (2006.01) |

(52) U.S. Cl.

CPC ............ *A61K 9/009* (2013.01); *A61F 2/2481* (2013.01); *A61K 35/28* (2013.01); *A61K 35/33* (2013.01); *A61K 35/34* (2013.01); *A61K 35/44* (2013.01); *A61K 45/06* (2013.01); *A61L 31/005* (2013.01); *A61L 31/16* (2013.01); *C12N 5/0697* (2013.01); *A61L 2300/414* (2013.01); *A61L 2430/20* (2013.01)

(58) Field of Classification Search

CPC .............................. A61K 9/009; A61F 2/2481

See application file for complete search history.

*Primary Examiner* — Marcia S Noble

(74) *Attorney, Agent, or Firm* — W&C IP

(57) ABSTRACT

The present invention relates to a pouch-like structure useful for mechanically preventing distension and/or resisting dilation of the heart and for supporting the hearts function by controllable and paracrine support of a failing heart in a mammal. The pouch-like structure is composed at least partly of engineered tissue comprising genetically engineered cells, such as genetically engineered cells other than cardiac myocytes whereby said genetically engineered cells contain a gene encoding a paracrine factor, said gene encoding the paracrine factor being under control of an inducible promoter system or a heterologous promoter system. Further, the present invention relates to a method for the preparation of the pouch-like structure for therapeutic, disease modelling, and drug development applications. In addition, the present invention relates to cells other than cardiac myocytes for use in the preparation of the pouch-like structure as described herein.

17 Claims, No Drawings

POUCH-LIKE STRUCTURE WITH PARACRINE ACTIVITY AND METHOD FOR ITS PREPARATION

FIELD OF THE INVENTION

The present invention relates to a pouch-like structure useful for mechanically preventing distension and/or resisting dilation of the heart and for supporting the hearts function by controllable and paracrine support of a failing heart in a mammal. The pouch-like structure is composed at least partly of engineered tissue comprising genetically engineered cells, like, genetically engineered cells other than cardiac myocytes whereby said genetically engineered cells, like genetically engineered cells other than cardiac myocytes, contain a gene encoding a paracrine factor said gene encoding the paracrine factor being under control of an inducible promoter system or an heterologous promoter system. Further, the present invention relates to a method for the preparation of the pouch-like structure, e.g. for therapeutic, disease modelling, and drug development applications as well as methods for treating individuals with the pouch-like structure according to the present invention. In addition, the present invention relates to cells other than cardiac myocytes for use in the preparation of the pouch-like structure as described herein.

BACKGROUND OF THE INVENTION

Heart failure is the leading cause of mortality globally with higher incidence in developed nations. Cardiac dilation is a common clinical phenomenon observed in several cardiac diseases, such as post-myocardial infarction and heart failure. While in the early stages, only portions of the heart may be affected. In advanced stages, the complete heart may be enlarged causing serious problems including arrhythmias or leakage of the cardiac valves. Cardiac dilation is a frequent reason for subjecting a patient to heart transplantation. Today various approaches have been proposed to reverse cardiac dilation including drug therapy, device therapy and cell-based therapy.

The drug-based therapy includes administration of beta-adrenergic receptor blockers. Drug therapy is a quite old approach to reverse pathologic effects of cardiac dilation. However, healing of myocardial dilation or heart failure cannot be achieved by drug therapy alone.

A further approach is device therapy. For example, to assist the failing heart cope with its pumping function, left ventricular assist devices can be implanted. Alternative device strategies include implantation of means restricting further dilation including bags. For example, WO 2008/058917 describes pouch-like constructs for preventing heart distension. Moreover, complete artificial hearts are under development, although not yet prepared for use.

Moreover, cell-based therapies are described in the art including the application of bone marrow derived mesenchymal stem cells as well as human pluripotent stem cells, including embryonic stem cells, induced pluripotent stem cells, pathogenic stem cells, and cardiac progenitor cells. However, sources and application thereof are limited. Moreover, experimental data show that paracrine support may have a therapeutic effect in cardiac dilation therapy. For example, it has been suggested to introduce IGF-1, however, a clear therapeutic benefit of systemically applied IGF-1 has not been demonstrated yet.

Quite recently heart muscle tissue engineering has come into the focus of scientists. Tissue engineering has been developed to biophysically support the failing heart, but also to provide in vitro tests for drug development and studies of organogenesis. With respect to heart muscle repair the main goals are to (i) add contractile elements to the failing heart for functional support and (ii) provide restraint similar to the approaches where bags are to be placed over the dilated heart, thus, restricting further dilation, but fully humanized. For example the use of scaffolds either in synthetic or biological environments and seeding cardiomyocytes have been used. WO 2008/058917 describes pouch-like constructs for preventing heart distension wherein engineered tissue is used for obtaining a pouch-like structure. Mammalian engineered heart tissues have been developed for drug screening and therapeutic applications, e.g. Zimmermann et al. Biotechnol. Bioeng. (2000), 68(1), 106 to 14. It was possible that the mammalian engineered heart tissues had coordinated beating with directed force development and heart muscle like physiology and pharmacological responses. The pouch-like structure described in WO 2008/058917 is based on said mammalian engineered heart tissue. This mammalian engineered heart tissue includes cardiomyocytes. The engineered heart tissue may also be obtained from heart tissue other than cardiomyocytes. For example, fibroblasts, smooth muscle cells etc. may be used.

However, despite the recent increased focus on developing advanced models of engineered tissues, several clinical challenges remain to be addressed: Engineered cardiac structures should be of a clinically relevant size and thickness and consist of immunologically tolerable cell populations in a matrix similar to the host heart. In addition, these structures must also be able to connect to the host blood supply, propagate electrical pulses which must be synchronised with the host myocardium and subsequently generate sufficient contractile force to aid in blood circulation.

BRIEF DESCRIPTION OF THE PRESENT INVENTION

The aim of the present invention is to provide new pouch-like structures for applications in heart failure treatment, disease modelling, drug development, and target identification as well as validation.

In a first aspect, the present invention relates to a pouch-like structure suitable for enclosing at least a part of the heart of a mammal, said pouch-like structure comprises an engineered tissue wherein at least a part of the engineered tissue comprises genetically engineered cells, such as genetically engineered cells other than cardiomyocytes, whereby said genetically engineered cells, contain a gene encoding a paracrine factor, said gene encoding the paracrine factor being under control of an inducible promoter system or a heterologous promoter system.

For example, the paracrine factor may be protein factors including different types of growth factors like IGF-1 but also other types of compounds having cardio protective or regeneration inducing properties on cardiac tissue, like nucleic acid molecules including miRNA.

The inducible promoter system or the heterologous promoter system may be a chemically inducible promoter system known in the art.

In a preferred embodiment the engineered tissue present in the pouch-like structure contains additionally cardiomyocytes.

In a further aspect, the present invention relates to a method for the preparation of a pouch-like structure suitable for enclosing at least a part of the heart of a mammal and comprising engineered tissue, said engineered tissue comprising genetically engineered cells, such as genetically engineered cells other than cardiac myocytes, which contain a gene encoding a paracrine factor and said gene being under control of an inducible promoter system or a heterologous promoter system, said method comprises the steps of a) providing a matrix having a recess in one surface of the matrix, saidrecess has appropriate dimensions to hold a defined reconstitution volume for the formation of the pouch-like structure,
b) providing a body having dimensions corresponding to the desired dimensions of the interior of the pouch-like structure to be formed, and positioning the body in the recess of the matrix such that the body is spaced from the walls of the recess to form a space between the body and the walls of the recess corresponding to the reconstitution volume needed for formation of a pouch-like structure,
c) positioning a reconstitution mixture in the recess, saidreconstitution mixture comprises mammalian cells, like allogenic cells, or autologous cells, and suitable scaffold material which can be incubated to form an engineered tissue structure comprising said cells,
d) incubating the reconstitution mixture until the tissue construct forms within the matrix recess between the body and the matrix,
e) exchanging the culture medium once the pouch-like construct has formed around the central body,
f) removing the body with the tissue construct adherent thereto from the matrix recess, and
g) separating the tissue construct form the body, wherein at least a part of the mammalian cells present in the engineered tissue structure are genetically engineered cells, such as, genetically engineered cells other than cardiac myocytes whereby said genetically engineered cells, contain a gene encoding a paracrine factor and said gene being under control of an inducible promoter system or a heterologous promoter system.

The present inventors recognized that genetically engineered cells, such as—genetically engineered cells other than cardiomyocytes, containing a gene encoding a paracrine factor are suitable to promote engraftment of the pouch-like structure and to improve the supportive activity on the heart tissue. The pouch-like structure according to the present invention is distinct to WO 2008/058917 firstly as to its design principle allowing easy size adaptation and secondly as to its controllable paracrine activity to support on the one hand the generation of human heart sized pouch-like structures in vitro and engraftment in vivo (by release of for example prosurvival [e.g. IGF-1], angiogenic [e.g. VEGF], and cardiogenic/regenerative [e.g. IGF-1, miR133]) factors) and on the other hand enhance performance of the adjacent myocardium. It is possible to enhance graft survival using appropriate factors being secreted (e.g. anti-apoptotic, angiogenic, inflammation modulating, cardioangiogenic factors).

DETAILED DESCRIPTION OF THE PRESENT INVENTION

In a first aspect, the present invention relates to a pouch-like structure suitable for enclosing at least a part of the heart of a mammal, said pouch-like structure comprises an engineered tissue characterized in that at least a part of the engineered tissue comprise genetically engineered cells, like, genetically engineered cells other than cardiac myocytes, whereby said genetically engineered cells, such asgenetically engineered cells other than cardiac myocytes, contain a gene encoding a paracrine factor said gene encoding the paracrine factor being under control of an inducible promoter system or a heterologous promoter system.

In this connection, the term "pouch-like structure" refers to a structure which surrounds at least a part of the heart. For example, the pouch-like structure is a bag-shaped structure having an opening and preferably a single-opening. In an embodiment, the structure is shaped in such a manner that it is suitable for enclosing and compressing at least a part of the heart of a mammal.

That is, the pouch-like structure is adapted to receive the heart of a mammal in such a manner that said structure is able to apply slight pressure on the surface of the heart wherein saidpressure prevents extension and/or resists dilation during systolic and diastolic activity of the heart. The pouch-like structure is able to adjust to the dimension of the part.

In an embodiment of the present invention, the structure embraces the ventricles of the heart which means that when applied to the surface of the heart the structure reaches from the Apex cordis to the Sulcus coronarius cordis which is the annular groove located between the ventricles and the atria. The structure can be applied to the outer surface of the heart in a manner that it is in direct contact with the epicardium of the heart. This procedure requires a removal of the pericardium. In another embodiment, the pericardium can remain intact and the pouch-like structure and can be applied on its outer surface. In a preferred embodiment, the structure is able to structurally integrate into the myocardium.

The term "mammal" as used herein includes all types of mammals, such asrodents including mice and rats as well as dog, cat, sheep, primate or human.

The term "engineered tissue" refers to a tissue obtained in vitro. Typically, the engineered tissue comprises support material also referred to as scaffold as well as cells. The engineered tissue is a tissue generated by in vitro tissue engineering techniques. The term "engineered heart tissue" or EHT means a tissue of a mammalian origin, like human or primate origin, which comprises mammalian cardiac derived cells obtained by tissue engineering techniques, for example engineered heart muscle (EHM).

The terms "cardiac myocyte" and "cardio myocyte" are used interchangeably and refer to an excitable cell composed of myofibrils that provide contractile force when stimulated, but is distinguishable from a skeletal muscle cell.

"Heart tissue" can also comprise fibroblasts, endothelial cells, smooth muscle cells, leucocytes including macrophages and other typically mononuclear cells besides cardiac myocytes.

Further, the term "paracrine factor" identifies factors, e.g. peptides, proteins as well as small molecules and nucleic acid based molecules including miRNA. Paracrine factors diffuse over a relative short distance representing a form of cell-to-cell communication whereby a cell produces a signatory induced change in nearby cells. Paracrine factors are secreted into the immediate extracellular environment of the producing cells, thus, acting locally on adjacent, but potentially also remotely depending on the strength of the paracrine gradient established by a given cell.

Typical examples of paracrine factors are members of the growth factor family including fibroblast growth factor (FGF), growth promoting factors, angiogenic factors or anti-apoptopic factors. Examples for such factors include but are not limited to VEGF, HGF, PLGF, PDGF, STF-1, IGF-1, FGF, HCG, BMP and others. These factors can induce angiogenesis, support heart cell survival, induce cell proliferation or hypertrophic growth.

Other compounds suitable as paracrine factors include local effecting molecules, in particular miRNA molecules. A suitable miRNA molecule includes miR-133, miR-1, miR-499, miR-208, miR-199A-3p, miR-590-3p, miR-1825, miR-33b.

The paracrine factors according to the present invention have cardio-protective and/or cardio-regeneration inducing activity. The skilled person is well aware of suitable paracrine factors.

The terms "comprise" or "comprising" or the terms "contain" or "containing" includes the embodiments of "consist" or "consisting of".

Further, the term pluripotent stem cells refers to pluripotent stem cells whereby said stem cells are not produced using a process which involves modifying the germ line genetic identity of human beings or which involves use of human embryo for industrial or commercial purposes.

The term "genetically engineered cell(s)" as used herein refers to a modified cell that includes one or more activities distinct from an activity present in a cell utilized as a starting point. A genetically engineered cell includes a heterologous polynucleotide in some embodiments, and in certain embodiments, a genetically engineered cell has been subjected to selective conditions that alter an activity, or introduce an activity relative to the starting cell.

In this connection, it is noted that the term "genetic engineered" or "genetically engineered" refers to a suitable nucleic acid addition, removal or alteration that facilitates production of a target product in the engineered cell.

The inducible promoter system according to the present invention may be a promoter system which may be induced by chemical means. Alternatively, the induction of the inducible system may be achieved by light, radiation, hypoxia, hypo—as well as hyperthermia and the like. Suitable systems for temporal and/or spatial induction are described e.g. in Guo Z., et al., Trends in Molecular Medicine, 14, 9, 410-418, 2008.

A preferred embodiment of the inducible promoter system according to the invention includes a chemically inducible promoter system, like the tetracycline-based system, the rapamycin-based systems, the progesterone-based systems, and the ecdysone-based systems. In this connection, the tetracycline-based system may be a TetOn or a TetOff system. The skilled person is well aware of the systems accordingly.

In another embodiment, the promoter system may be a heterologous promoter system. The term "heterologous promoter system" refers to a promoter system which is not present naturally in the cell, e.g. not present in the chromosome of the engineered cell.

In an embodiment of the present invention, the pouch-like structure is a structure comprising engineering tissue wherein the genetically engineered cells, like, genetically engineered cells other than cardiac myocytes, are cells selected from fibroblasts, smooth muscle cells, endothelial cells, mesenchymal stem cells, cardiac stem cells, pericytes, and leucocytes or precursor cells of said cells or pluripotent stem cells, wherein said pluripotent stem cells are not produced using a process which involves modifying the germ line genetic identity of human beings or which involves use of a human embryo for industrial or commercial purposes. It is preferred that fibroblasts or mesenchymal stem cells or precursor cells are used. For example, suitable cells can be obtained from skin or gingiva biopsies, liposuction material, heart biopsies, bone marrow, or blood.

In an embodiment of the present invention, the genetically engineered cells, such asgenetically engineered cells other than cardiac myocytes, are allogenic cells. In an embodiment, it is preferred that the engineered cells, such as genetically engineered cells other than cardiac myocytes, are autologous cells of the subject expected to receive the pouch-like structure according to the present invention.

That is, the engineered cells, such as genetically engineered cells other than cardiac myocytes, are obtained in advance from the subject, genetically engineered in vitro by introducing the gene encoding the paracrine factor whereby said gene encoding the paracrine factor is under control of an inducible promoter system or a heterologous promoter system. The system may require the introduction of a second plasmid into the cells, for example, as described for the tetracycline-based system.

In another embodiment, the engineered tissue comprises additionally myocytes, like cardiac myocytes and/or other cells of the heart tissue other than cardiac myocytes. The myocytes may be derived from progenitor cells or precursor cells preferably obtained from the subject expected to receive the pouch-like structure. Said myocytes may be non-modified or genetically engineered myocytes. However, it is also possible that no myocytes or precursor cells thereof are present in the pouch-like structure according to the present invention.

When myocytes are present in the engineered tissue of the pouch-like structure according to the present invention, the structure has contractile properties.

The heart tissue can comprise fibroblasts, endothelial cells, smooth muscle cells, leucocytes including macrophages and other cells of mononuclear origin beside cardiac myocytes.

In general, the pouch-like structures of the invention can be generated from muscle and non-muscle cells as well as from mixtures of muscle and non-muscle cells. Muscle cells may include primary and stem cell derived cardiac myocytes as well as primary and stem cells derived skeletal and smooth muscle cells. It is preferred that stem cell or reprogramming-derived cardiac myocytes are used for engineering the tissue structure when said cardiac myocytes are present.

For engineering the pouch-like structure including the engineered tissue, a scaffold substance, such as collagen is mixed with culture medium and the pH is adjusted accordingly. Matrigel may be added to said solution, e.g. with a final concentration of 5 to 15%. The mixture is then added to a cell suspension of the cells to be present in the engineered tissue to obtain a reconstitution mixture at suitable culture conditions.

According to the present invention, the reconstitution mixture includes genetically engineered cells, such as genetically engineered cells other than cardiac myocytes, containing the gene encoding for paracrine factors.

The invention further provides a method for the preparation of a pouch-like structure suitable for enclosing at least a part of the heart of a mammal and comprising engineered tissue, said engineered tissue comprising genetically engineered cells, like, genetically engineered cells other than cardiac myocytes, which contain a gene encoding a paracrine factor and said gene being under control of an inducible promoter system or an heterologous promoter system, said method comprises the step of a) providing a matrix having a recess in one surface of the matrix, which recess has appropriate dimensions to hold a defined reconstitution volume for the formation of the pouch-like structure, b) providing a body having dimensions corresponding to the desired dimensions of the interior of the pouch-like structure to be formed, and positioning the body in the recess of the matrix such that the body is spaced from the walls of the recess to form a space between the body and the walls of the recess corresponding to the reconstitution volume needed for formation of a pouch-like structure, c) positioning a reconstitution mixture in the recess, which reconstitution mixture comprises mammalian cells, like allogenic cells, or autologous cells, and suitable scaffold material which can be incubated to form an engineered tissue structure comprising said cells, d) incubating the reconstitution mixture until the tissue construct forms within the matrix recess between the body and the matrix, e) exchanging the culture medium once the pouch-like construct has formed around the central body, f) removing the body with the tissue construct adherent thereto from the matrix recess, and g) separating the tissue construct from the body, wherein at least a part of the mammalian cells present in the engineered tissue structure are genetically engineered cells, such as, genetically engineered cells other than cardiac myocytes, whereby said genetically engineered cells, contain a gene encoding a paracrine factor and said gene being under control of an inducible promoter system or a heterologous promoter system.

Thus, according to the method of the present invention, a matrix with a recess in one surface and a body are provided, the body is disposed in the recess, and a reconstitution mixture is introduced into the recess in order to form the pouch-like construct from the tissue cells of the reconstitution mixture in the space between the outer surface of the body and the inner surface of the matrix walls defining the recess. The matrix together with the body surface is a mold. As used herein, the term matrix designates any body having a recess or cavity used for shaping an object or material and is e.g. a mold or a part of a mold. In a preferred embodiment the matrix is a non-porous solid material. This has the advantage not to impede outflow of reconstitution mixture from the recess into a porous matrix as described in WO 2008/058917. Furthermore, no additional culture medium aside from the medium contained needs to be added. Thus, by overcoming said technical problems, the method of the present invention provides an easily scalable method.

Within the meaning of the present invention, the term “reconstitution mixture” designates a mixture comprising mammalian cells including genetically engineered cells, such as genetically engineered cells other than cardiac myocytes whereby said genetically engineered cells contain a gene encoding a paracrine factor and said gene being under control of an inducible promoter system or an heterologous promoter system together with suitable scaffold material which can be incubated to form an engineered tissue structure. The reconstitution mixture is for generating the engineered tissue, like engineered heart tissue, and are described e.g. in WO 2008/058917.

In another embodiment multiple layers of reconstitution mixtures are cast around the consolidated core pouch-like structure to form thicker engineered tissues.

That is, the present invention allows for easily scalable pouch-like structures. In an embodiment of the present invention, the method according to the present invention is conducted using a solid non-porous matrix body, thus, no additional culture medium aside from the culture medium contained in the reconstitution mixture is required. By using the inner inflatable and deflatable balloon body, controlled mechanical stimulation is possible and the genetically modified engineered cells allows release of suitable paracrine factors for therapeutic, cardiogenic and regenerative treatment of the heart.

For example, the body is an inflatable structure such as an inflatable balloon which is connected with means for effecting a precisely controlled inflation of the body. By controlling the inflation, for example by using a suitable pump, the dimension of the balloon forming the body can be precisely adjusted so that the space between the body and the walls of the recess and, ultimately, the wall thickness and the interior dimensions of the engineered tissue structure can be adapted to the particular application. The balloon may be inflated and deflated during or after the formation of the structure at a given rate and rhythm, e.g. sinus rhythm. This would allow simulation of physiological loading and unloading of a ventricle and can improve the morphological and functional properties of the tissue structure and allow force measurement by the technique pressure change in the balloon developed by this spontaneously constructing tissue structure.

That is, the structure of the present invention may be subjected to tensile strength, for example, said tensile strength is static, phasic or auxonic stress or a combination thereof. Suitable methods are described e.g. in WO 2008/058917 or WO 01/55297 which are incorporated herein by reference.

In addition, in the method according to the present invention step b) may be performed prior to or after step c) as described above.

In addition, the present invention relates to a method of treating a disease which is associated with dilation and functional deterioration of the heart of a mammal or which is associated with diseased heart cells, pathological remodelling of the heart stroma including but not limited to extracellular matrix and vasculature. The treatment comprises the steps in which the pouch-like structure according to the present invention is applied to the surface of the heart in order to prevent distension and/or resisting dilation of the heart and/or to support regeneration of diseased heart cells by paracrine factors. Preferably, the mammal is a human. The treatment may include removal of the pericardium in advance.

Moreover, the present invention relates to the use of the pouch-like structure according to the present invention for disease modelling, drug development, and drug target identification as well as validation.

Finally, the present invention relates to the cells other than cardiac myocytes for use in the preparation of a pouch-like structure suitable for enclosing at least a part of the heart of a mammal wherein said non-cardiac cells are genetically engineered cells containing a gene encoding a paracrine factor and/or a gene encoding RNA like miRNA, and said gene being under control of an inducible promoter system.

For example, the cells other than cardiac myocytes for use according to the present invention are cells selected from fibroblasts, smooth muscle cells, endothelial cells, mesenchymal stem cells, cardiac stem cells, pericytes, and leucocytes or precursor cells of said cells or pluripotent stem cells, wherein said pluripotent stem cells are not produced using a process which involves modifying the germ line genetic identity of human beings or which involves use of a human embryo for industrial or commercial purposes.

The engineered cells may be engineered cells including the inducible promoter systems, for example a chemically inducible promoter system as described herein. The skilled person is well aware of suitable systems applied in humans or other mammals.

The cells other than cardiac myocytes for use according to the present invention are particularly allogenic or autologous cells of the subject expected to receive the pouch-like structure according to the present invention.

The present invention will be described by further examples without limiting the same thereto.

EXAMPLES

Preparation of Cells

For the construction of engineered heart tissue either as human EHM (as for example described in Soong et al. Current Protocols in Cell Biology (2012) 23.8.1-23.8.21) and BioVADs (biological ventricular assist device, Yildirim et al. Circulation (2007), 116:I-16-I-23) with paracrine activity (paraBioVAD) cardiomyocytes and non-myocytes are needed. For the construction of non-contractile pouch-like tissue with paracrine activity (paraPouch) only non-myocytes are needed. Cardiomyocytes are typically derived from pluripotent stem cells or direct programming. Non-myocytes (i.e. typically mesenchymal cells) are from skin or gingiva bopsies, liposuction material, heart biospies, bone marrow, or blood. Here, human pluripotent stem cell derived cardiomyocytes and foreskin fibroblast with and without genetic modification (i.e. Tetinducible IGF-1 expression) were used as an example and mixed into a collagen-hydrogel with culture medium (2×DMEM) to form a EHM, paraBioVAD, or paraPouch reconstitutions mixture (Table 1).

TABLE 1

Composition of reconstitution mixture

| Reconstitution mixture* | 4x EHM | 1x paraBioVAD | 1x paraPouch |
|---|---|---|---|
| Collagen-hydrogel (3.2 mg/ml) | 440 µl | 2,200 µl | 2,200 µl |
| 2X DMEM | 535 µl | 2,675 µl | 2,675 µl |
| **NaOH 0.1N | 95 µl | 475 µl | 475 µl |
| ***Matrigel ® | 200 µl | — | — |
| ****Cell Number (adapt volume) | $6 \times 10^6$ | $26 \times 10^6$ | $10 \times 10^6$ |
| *****TOTAL VOLUME | 2,100 µl | 8,400 µl | 8,400 µl |

*Can be adapted according to the target dimension of the EHM, paraBioVAD (rat heart sized), or paraPouch (rat heart sized).
**NaOH 0.1N is added until the pH indicator (phenol red) suggests a pH of 7.2-7.6. Given volumes need to be adapted according to the indicator readout, but are typically within plus/minus 20 µl of the indicated volumes.
***Matrigel can be left out completely without compromise in EHM, paraBioVAD, or paraPouch function.
****Cell suspension contains cardiomyocytes and HFF (75%:25%; EHM, para-BioVAD) or 100% HFF. Cell number can be adapted as needed. Volume of cell suspension has to be adapted according to the target TOTAL VOLUME.
*****TOTAL VOLUME can be increased or decreased as needed as long as constituents are increased and decreased proportionally.

Construction of Engineered Tissue

Cells as single cell suspension were mixed thoroughly with collagen, 2×DMEM, NaOH and in the case of EHM with Matrigel in a prechilled 15 ml centrifuge tube accordingly (Table 1). NaOH was added dropwise until Phenol red color indicator changes from yellow (acidic) to pink. For EHM 450 µl of the reconstitution mix (Table 1) was quickly distributed into individual casting molds and placed in a 37° C. humidified incubator with 5% $CO_2$ for 1 hour. Following that, 6 ml of prewarmed complete EHM medium was overlayed until all EHMs were completely covered with medium and then incubated for a further 24 hours and medium was exchanged thereafter every other day. After the EHMs had progressively condensed, typically after 3 days, they were transferred onto resilient silicone holders (Soong et al. Current Protocols in Cell Biology (2012) 23.8.1-23.8.21).

Prior to the transfer of condensed EHMs, the necessary number of silicone holders were first placed into a tissue culture plate filled with EHM medium. Thereafter, the top of the removable silicone tubing of a casting mold dish was pinched gently with a pair of curved forceps and slowly removed from the casting dish. Next, the silicon tube was placed over one of the paired silicone poles of a silicone holder and the EHM was released by gentle shaking or nudging with a pipette tip. With the help of another sterile pipette tip, the other silicone pole was gently bent to suspend the EHM between the 2 poles. The contracting EHM will bend the silicone holders inducing dynamic load for the EHM to work against. Medium was exchanged every 2 days over the next 7 days of EHM maturation. EHMs were ready for end-point analyses on culture day 10.

Isometric Force Measurements

Force measurements of EHMs were performed in thermostatted organ baths (FMI GMbH) as previously described. Briefly, after day 7 of EHM culture on silicone stretchers, EHMs were carefully removed and placed over the hooks of a force transducer in an organ bath filled with Tyrode's solution (Zimmermann et al. Biotechnol. Bioeng. (2000) 68(1):106-14). EHMs were field stimulated via two platinum electrodes at 2 Hz (5 ms monophasic pulses, 200 mA) and preloaded to the length of maximal force production (Lmax). The response to increasing calcium concentrations (0.2 to 4 mmol/L) data were acquired using BMON software and analyzed by AMON software (both Jäckel; Hanau, Germany).

Dissociation of EHM for Flow Cytometry

To obtain cells from EHMs for flow cytometry, each EHM was cut into half and incubated in 1 ml of collagenase for 30 minutes at room temperature. Thereafter, the remaining large pieces were gently teased apart with two 27G needles to obtain smaller pieces in the cell culture well. Next, further enzymatic dissociation of the pieces was performed. After single cells were obtained from the dissociation of EHMs, the cells were fixed in 70% EtOH and kept in 4° C. until flow cytometry.

Construction of ParaBioVAD and ParaPouch Molds

Modifications of the original rat BioVAD protocols (Yildirim et al. Circulation (2007), 116:I-16-I-23) were required to create a scalable casting mold for the generation of large human paraBioVADs and paraPouches. In addition, to confer a biomimetic culture format with regular pulsatile action, an inflatable inner structure required to be designed.

A series of casting cubes from Makrolon® (Bayer MaterialScience) were spherically machine-hollowed out and aligned to generate 18 mm, 20 mm and 30 mm casting molds. 10% molten agarose was poured into the 18 mm casting mold and cooled to form a solidified spherical agarose ball and speared with a central wooden spine. Next, the ball and stick was removed, centrally placed in a 20 mm casting mold and liquid silicone (Silicone 2000 and curing agent 9:1 ratio) was poured around the 18 mm agarose ball and allowed to cure uniformly for 24 hours at room temperature. Thereafter, the solidified silicone coated ball and stick were removed and placed in boiling water until the inner agarose dissolved, yielding an inflatable sphere with 20 mm outer diameter and a wall thickness of 1 mm. This 20 mm inflatable sphere was then placed in a 30 mm casting mold and connected to a 10 G silicone urinary catheter (BARD, USA).

Preparation of Casting Molds for Biomimetic Support

First, the silicone sphere was connected to a mechanical animal ventilator (FMI, GmbH) and inflated to check for surface tears so as to ensure proper pulsatile function. Next, the casting blocks with attached silicone spheres were boiled, drained and autoclaved to sterilize the whole apparatus prior to use. After cooling down to room temperature, the BioVAD casting mold could then be used for the seeding of the reconstitution mix.

Human ParaBioVAD and ParaPouch

Single cell mixtures were combined with culture medium (2×DMEM) and pH-neutralized collagen (Table 1). The ice-cold (4° C.) reconstitution mixture was triturated thoroughly on ice and then transferred quickly into the molds to facilitate formation of a pouch-like tissue construct (similar for paraBioVAD and paraPouch). Additional culture medium was added after 24 h and then exchanged every other day. From culture days 3 to 8, uniform pulsatile stretch (10% strain, 90 beats per minute) was initiated using a mechanical ventilator to inflate and deflate the central sphere. Non-pulsatile conditions served as control (0% strain).

Histology

Parafin sections were prepared after fixation of tissue in 4% formaldehyde (Histofix, Roth) overnight. This was followed by hematoxylin and eosin staining following standard protocols (Zimmermann et al. Circulation Research (2002) 90(2):223-30).

Construction of IGF-1 Encoding Lentivirus

The plasmids pCMV-XL4 (SC119792; Origene), pLVx-Tight-Puro and pTetOn (both Lenti-X™ TetOn® Advanced inducible expression system, 632162; Clontech) were purchased and used in the development of cell based IGF-1 secretion. pCMV-XL4 consists of the full length human IGF-1 transcript; pLVx-Tight-Puro is an expression response vector which consists of a modified CMV promoter (PTight) with regulatory elements of the tetracycline operator sequences and includes a puromycin resistance gene; pTet-On-Advanced is the transactivator plasmid which contains an improved version of the reverse tetracycline controlled transactivator protein (rtTA), and also includes a neomycin resistance gene. First, the plasmid pLVx-Tight-Puro was digested with restriction enzymes Notl and Xbal (both FastDigest®, Fermentas) in a double digestion reaction to generate a linearized plasmid (linpLVx-Tight-Puro). The restriction reaction mix included: 1.0 μl Notl, 1.0 μl Xbal, 2 μl FastDigest® Buffer, 1 μg/μl plasmid pLVx-Tight-Puro. This was incubated at 37° C. for 4 hours and subsequently heat inactivated at 85° C. for 5 minutes. The restriction digest product was separated on a 1% agarose gel, visualized by EtBr staining, excised and purified. The purified linearized linpLVx-Tight-Puro vector was stored at −20° C. until required.

Next, a mastermix reaction containing 250 ng purified human IGF-1 amplified product, 100 ng linpLVx-Tight-Puro, 4 μl rapid ligation buffer (5×), 1 μl T4 DNA ligase (5 units/μl) was assembled and incubated at room temperature for 10 minutes to generate the recombinant pLVx-Tight-hIGF1-Puro plasmid.

Then, chemically competent DNA methylase negative (dam-) *E. coli* strain (One Shot®INV110; Invitrogen) was chemically transformed with 2 μl pLVx-Tight-hIGF1-Puro plasmid according to the manufacturer's protocol. Positive colonies containing the ligated plasmid were selected for by ampicillin resistance and further confirmed by colony PCR with hIGF-1 primers listed above. Briefly, one colony of transformed *E. coli* was picked and inoculated into a tube containing the same PCR master mix and PCR amplified. Amplification of a positively transformed *E. coli* colony containing the plasmid was then performed by sterile loop inoculation of a single colony into a 2 L glass conical flask containing 250 ml of LB medium supplemented with 100 μg/ml ampicillin in a 37° C. shaking incubator (Innova 4300) with constant 200 rpm agitation for 24 hours. Next, the amplified pLVx-Tight-hIGF1-Puro plasmid was extracted and purified according to the manufacturer's protocol for maximum pure plasmid recovery (NucleoBond® Xtra Maxi; Macherey-Nagel). The purified ligated plasmid was stored in −20° C. until required.

Lentivirus Production

To generate IGF-1 encoding lentivirus, TSA cells were transfected with 3 μg of pLVx-Tight-hIGF1-Puro, 2 μg of pCMV2.1 and 3 μg pMD2G plasmids (Trono Lab, EPFL, Switzerland) using lipofection with Polyfect (Qiagen). The cell culture medium was changed after 16 hours and medium containing recombinant IGF-1 lentiviral particles were harvested 48 hours later. The LentiX™ Go Stix™ (Clontech) was used according to the manufacturer's protocol to determine the titer of >5×10$^6$ IFU/ml of the lentiviral particles.

To generate the virus containing the Tet-On transactivator, TSA cells were also used as host cells and transfected with the same technique as described above. Again, cell culture medium was changed after 16 hours and medium containing recombinant Tet-On lentiviral particles were harvested 48 hours later. Both hIGF-1 and Tet-On lentivirus were then stored in −80° C. freezer until required.

Lentiviral Transduction of Human Foreskin Fibroblasts

Prior to transduction of HFF with the lentiviruses, fresh cell culture medium with 0.5% FBS was exchanged and supplemented with 10 μg/ml hexadimethrine bromide (polybrene, Millipore) at 37° C. for 10 minutes. Polybrene is a cationic polymer, which neutralizes cell membrane charges and increases the efficiency of transduction of viruses when added to cell culture medium. Thereafter, conditioned cell medium from TSA cells containing recombinant IGF-1 lentivirus was layered over HFF cells cultured in a 100 mm cell culture plate in a dropwise manner and then incubated in a 5% $CO_2$, 37° C. cell culture incubator for 72 hours. Thereafter, fresh HFF medium with 15% FBS was exchanged and supplemented with 10 ng/ml basic Fibroblast Growth Factor (bFGF; Miltenyi) and 1 μg/ml Puromycin (Invitrogen). After 7 days, surviving cells were selected as $HFF^{hIGF1+}$ cells.

To generate a stable inducible secretion of human IGF-1 from HFF cells, the $HFF^{hIGF1+}$ cells were next transduced with pTet-On-Advanced lentivirus as outlined above followed by extended culture in medium containing 1 μg/ml puromycin and 800 μg/ml neomycin (Invitrogen) for 7 days. Cells that survived double antibiotic selection were deemed successfully transduced with both hIGF-1 and Tet-On viruses to generate the inducible human IGF-1 cell line: $HFF^{hIGF1+TetOn+}$. These cells were amplified to a desired quantity and frozen down as stock cell cultures in −80° C. until required.

Analysis of IGF-1 Expression and Secretion

Supernatants from transfected cells and untransfected cells were harvested and stored in −20° C. until further use. To obtain cell lysates from these cultures, cells were rinsed thoroughly with PBS to avoid supernatant contamination. Next, 400 μl CytoBuster protein extraction buffer (Novagen) was layered over the cells and allowed to incubate on ice for 30 minutes. Thereafter, with the help of a cell scraper, the lysates were collected individually in 1.5 ml microfuge tubes and centrifuged at 12,000×g for 30 minutes to pellet the cell debris. The supernatant above this cell debris was then collected into sterile microfuge tubes and designated as cell lysates and stored at −20° C. until further required.

ELISA Detection of IGF-1

IGF-1 concentration in cell culture supernatants was measured with a sandwich enzyme linked immunosorbent assay (ELISA) following the manufacturer's protocol (Quantikine® human IGF-1; R&D systems). Results were recorded at 450 nm and analysed with a microplate reader (FlexStation 3; Molecular Devices).

Western Blot Detection of AKT and Phospho AKT

Cell lysates were first quantified with standard Bradford protein assay to standardize loading protein concentrations and processed using standard western blot protocols. Briefly, proteins were resolved on a 10% SDS-polyacrylamide gel followed by 400 mA electrophoretic transfer to a 0.2-0.4 μm nitrocellulose membrane (Protran, Whatman) at 400 mA for 1 hour. All membrane blots were blocked with blocking buffer (5% goat serum in PBS) for 1 hour followed by incubation with primary antibodies against AKT and Phospho(Ser473)-AKT (both Cell Signalling; 1:1,000) and GAPDH (Santa Cruz, 1:1,000) overnight at 4° C. Thereafter, the membrane was washed with 1% TBST buffer (Appendix) thoroughly and incubated with secondary antibodies (goat anti-mouse IgG, 1:20,000) for 1 hour at room temperature. To visualize the protein bands, the membrane was incubated with horseradish peroxidase substrate (SuperSignal West Femto kit; Pearce, Thermo Scientific) and developed with a membrane detection system (VersaDoc; Bio-Rad) and analyzed with Quantity One software (BioRad).

Assambly of Human ParaBioVAD (ParaBioVAD)

To confer the paracrine modality to the hBioVAD, 18.2×$10^6$ hESC derived cardiomyocytes and 7.8×$10^6$ $HFF^{hIGF1+TetOn+}$ cells were mixed together to generate a paraBioVAD as highlighted in Table 1 and allowed to condense overnight. Thereafter, the paraBioVAD was allowed to condense further for another 9 days prior to implantation.

Implantation of Human ParaBioVAD in Wistar Rat

The paraBioVAD was implanted into a 450 g male Wistar rat (Charles River). The implantation was performed under isoflurane (4%) anaesthesia. The heart was exposed after median sternotomy and careful refraction of pericardium. Next, the paraBioVAD was slipped over the hearts, enveloping the apex, left and right ventricles and secured with 2 sutures (6-0 prolene, Ethicon). Following closure of sutures, cyclosporine A (5 mg/kg) and methylprednisolone (2 mg/kg) were administered daily subcutaneously to suppress the immune response.

Statistics

GraphPad Prism software (GraphPad Software Inc; San Diego) was used to convert data sets into graphs (displayed as mean±SEM) and subjected to Student's t-test, one-way, or two-way ANOVA test where appropriate. P<0.05 was considered to be significant.

Results

To demonstrate the reliability and functionality following transduction of HFF cells with this Tet-On lentiviral transduction system, the inventors quantified the levels of human IGF-1 protein in the 72 hour conditioned supernatants and cell lysates harvested from $HFF^{wt}$ and transduced $HFF^{hIGF1+TetOn}$ with and without doxycycline exposure. Different concentrations of doxycycline were tested (10-100 ng/ml). the inventors observed that in the supernatants of non-stimulated $HFF^{hIGF1+TetOn}$ cells, human IGF-1 protein levels were secreted at approximately 2.8 ng/ml of medium while $HFF^{wt}$ cells secreted only 0.4 ng/ml IGF-1 protein. In cell lysates from $HFF^{wt}$ and $HFF^{hIGF1}$ cells, minimal human IGF-1 protein was detected (0.16 ng/ml and 0.23 ng/ml respectively). Exposure to doxycycline stimulation led to a 10 fold increase of human IGF-1 protein in the supernatants and cell lysates of $HFF^{hIGF1+TetOn}$ cells, while minimal IGF-1 protein was detected from $HFF^{wt}$ cells (Table 2). Increasing the doxycycline concentrations did not significantly increase IGF-1 protein production.

TABLE 2

Quantification of human IGF-1 protein (in ng/ml) from $HFF^{wt}$ and stably transduced $HFF^{hIGF1+TetOn}$ cells with and without doxycycline exposure.

| Doxycycline (ng/ml) | | 0 | 10 | 30 | 100 |
|---|---|---|---|---|---|
| $HFF^{wt}$ | Supernatant | 0.39 | 0.40 | 0.39 | 0.38 |
| | Cell Lysate | 0.16 | 0.16 | 0.17 | 0.16 |
| $HFF^{hIGF1+TetOn}$ | Supernatant | 2.77 | 20.29 | 19.58 | 20.07 |
| | Cell Lysate | 0.23 | 20.35 | 20.38 | 20.04 |

The downstream mediators of paracrine action of secreted IGF-1 on hypertrophy signaling pathway in hESC-derived cardiomyocytes was examined. 72 hour serum-free conditioned medium from unstimulated and doxycycline stimulated $HFF^{wt}$ and $HFF^{hIGF1+TetOn}$ cells were harvested and layered over day 16 hESC-derived cardiomyocytes for 30 minutes. The cardiomyocytes were then harvested and lysed. Western blot analysis of the hESC cardiomyocytes lysates revealed that phosphorylated Akt (pAkt) proteins were higher in unstimulated and stimulated $HFF^{hIGF1+TetOn}$ cells compared to $HFF^{wt}$ cells.

In this experiment, biological activity of transgenically expressed IGF-1 was confirmed. IGF-1 released from genetically modified human foreskin fibroblasts (HFF) induces Akt phosphorylation in cardiomyocytes. Western blot analyses of pAkt, Akt and GAPDH in hESC-derived cardiomyocytes exposed to supernatant from $HFF^{wt}$ (wild type) and $HFF^{IGF1+TetOn}$ (±10 ng/ml doxycycline stimulation) was performed. A summary of the Western blot (n=3 per group). *p<0.05 vs $HFF^{wt}$ (±doxycycline; two-sided, unpaired Student's t-test) was prepared.

To test the specific efficacy of doxycycline-induced IGF-1 release on heart muscle, the inventors supplemented EHMs with 20% of either $HFF^{wt}$ or $HFF^{hIGF1+TetOn}$ cells. Subsequently, EHMs were transferred onto flexible silicone poles on culture day 3. On culture day 7, 10 ng/ml doxycycline was added to the EHMs medium to induce hIGF-1 secretion from HFF cells. Control EHMs were left without doxycycline. EHMs were subjected to force measurements 72 hours later. Analyses of the forces revealed that, despite no doxycycline stimulation, EHMs generated with $HFF^{hIGF1+TetOn}$ cells developed stronger contraction forces compared to EHMs generated with $HFF^{wt}$ cells. However, doxycycline supplemented EHM with $HFF^{hIGF1+TetOn}$ cells developed highest forces compared to all other EHM groups across varying calcium concentrations, with maximum force at 3.2 mmol/L $Ca^{2+}$.

In this experiment, it was confirmed that transgenically expressed and pharmacologically induced IGF-1 supports heart muscle performance. Efficacy of drug (doxycylcine)-induced IGF-1 release was confirmed in engineered heart muscles (EHMs) by isometric contraction force measurements. Superiority of the "$HFF^{IGF1+TetOn}$+10 ng/ml doxycycline" group to the "$HFF^{IGF1+TetOn}$ without doxycycline", "$HFF^{wt}$", and "$HFF^{wt}$+10 ng/ml doxycycline" groups was confirmed. The ordinate displays twitch tension in mN. The abscissa denotes extracellular calcium concentrations. *$p<0.05$ vs $HFF^{wt}$ EHM; two-way ANOVA.

The inventors then enzymatically digested these human EHMs, isolated single cells and analyzed the cell sizes from each group using flow cytometry and observed that cells were larger in the presence of human IGF-1.

In this experiment, cardiomyocyte and non-myocyte response to IGF-1 release was confirmed. Released IGF-1 induced cardiomyocyte and non-myocyte hypertrophy in EHMs was shown. Cell size was measured by flow cytometry. *$p<0.05$ vs $HFF^{wt}$.

Enhanced size of non myocytes may be due to the addition of "large" $HFF^{hIGF1+TetOn}$. In contrast, cardiomyocyte hypertrophy seems to be stimulated by the HFFs paracrine activity. The inventors performed whole mount immuno-fluorescence staining on both groups of EHMs and observed that cardiomyo-cytes were generally elongated and anisotropically aligned and form cardiac bundles. However, EHMs generated from cardiomyocytes mixed with $HFF^{hIGF1+TetOn}$ appear to contain thicker muscle bundles and enlarged cardiomyocytes.

To finally prepare the BioVAD with paracrine IGF-1 release, 20% $HFF^{hIGF1+TetOn}$ were added to the BioVAD reconstitution mixture. This yielded paraBioVAD with similar appearance as the "simple" BioVAD.

A single paraBioVAD was implanted in an immunosuppressed Wistar rat and harvested after 3 weeks. The explant was observed to have contracted towards the apex but remain attached and still encompassed the ventricles. The inventors then performed routine Haematoxylin & Eosin (H&E) and Sirius Red stainings to study the morphology of the explanted paraBioVAD relative to the rat heart and observed that the paraBioVAD generally remained intact over the rat heart.

A clear border zone between the heart and the paraBioVAD was observed. Generally, a gap of 50-100 µm distinguishes the heart from the paraBioVAD. However, in several areas, there were clear "contact zones" between the paraBioVAD and recipient myocardium. "Myocardial-like" elongated cells were also observed. Interestingly, several areas showed developing vascular structures, suggesting early vascularization.

In this experiment, Proof-of-feasibility for cardiac engraftment of the engineered pouch-like construct provided by histological assessment after implantation of a paraBioVAD (denoted as BioVAD) on a rat heart was provided. Grafting areas of BioVAD to the rat heart was shown. A magnified area of engraftment with rat myocardium demonstrating survival of BioVAD containing cardiomyocytes was shown. Vascularization of BioVAD graft was shown and the developing vasculature was highlighted. A magnified image of vessels containing erythrocytes in BioVAD graft was shown. This finding provides evidence for an established connection of the recipients circulatory system to the graft.

The inventors reasoned that pharmacologically controlled paracrine secretion of IGF-1 could confer an additional therapeutic benefit to the BioVAD technology. To achieve this, a fibroblast cell line with stable IGF-1 secretion under the control of the Tet-On activator domain was generated. However, already under unstimulated conditions IGF-1 release was enhanced, but could be further enhanced by doxycycline supplementation. In these cells IGF-1 secretion reached maximum concentration already under 10 ng doxycycline. This was unexpected and either argues for an all-or-nothing activation, the need to test even lower doxycycline concentrations or insufficient linearity of the IGF-1 ELISA. Finally, alternative drug-inducible systems may need to be exploited to enable full control of IGF-1 release.

Half-maximal activation (EC50) of the IGF-1 receptor is at 2 ng/ml IGF-1. IGF-1 transduced cells supplemented the culture medium with 20.3 ng/ml IGF-1 in 30 minutes. The inventors also observed hypertrophy in IGF-1 expressing fibroblasts, which could be either an indirect effect of the transgenic approach or due to autocrine stimulation.

IGF-1 has been studied extensively in skeletal muscle biology and its effects on aging. Circulating IGF-1 produced from the liver typically activates PI3K/AKt/mTOR and MAPK pathways. Its effects on cardiomyocytes are mainly enhanced survival and hypertrophy; both are likely in response to AKT-activation. Different IGF-1 isoforms have been implicated in cardiomyocyte biology. In this study, IGF-1 variant 4 was overexpressed to activate prosurvival and physiological hypertrophy in EHMs. Conditioned medium from human IGF-1 secreting fibroblasts increased Akt phosphorylation in hESC-derived cardiomyocytes in a paracrine manner. These cardiomyocytes were also significantly bigger than those not exposed to IGF-1 suggesting hypertrophic gene activation program.

In three dimensional human cardiac tissue constructs, the inventor's resuits demonstrated that IGF-1-enriched EHMs developed enhanced contractile forces compared to non IGF-1-enriched EHTs. Here doxycycline addition to enhance IGF-1 release did indeed further improve contractile force. This model reflects better than a classical monolayer culture experiment (as performed for the first screen for biological activity) the complex in vivo environment with its considerable diffusion and unspecific peptide binding issues. Thus the presented EHM data provides first proof-of-concept for the proposed heart tissue support concept via paraBioVADs or paraPouches.

Given that IGF-1 plays a key role in many signaling pathways including proliferation, differentiation and hypertrophy, it would not be surprising that IGF-1 levels may be responsible for the regulation of contraction forces. Indeed, several studies have demonstrated that IGF-1 binds to receptor tyrosine kinase and activates Akt via PI3K, and enhances L-type $Ca^{2+}$ current channels. Moreover, Akt overexpression studies in the myocardium also suggest an increased calcium channel activity in ventricular myocytes.

Finally, the inventors integrated the IGF-1 releasing fibroblasts into the human BioVAD system to test the feasibility of paraBioVAD implantation. The paraBioVADs were generated with 20% $HFF^{hIGF1+TetOn}$ cells. Importantly, the recipient rat survived the operation with no evidence of pericardial constriction or other complications. Teratoma formations were not detected.

Following explantation of the rat heart, histological stainings revealed areas of paraBioVAD that resemble myocardial structures. There was clear survival of cells within the graft which are elongated and aligned at the borderzone, confirming that such engineered cardiac constructs can survive after transplantations in agreement with other studies.

The inventors were encouraged by the observation of vascularization in several areas within the paraBioVAD. Indeed, vascularization is a critical point in attempts to generate humanized cardiac tissue constructs.

REFERENCES

Throughout this application, various references describe the state of the art to which this invention pertains. The disclosures of these references are hereby incorporated by reference into the present disclosure.

The invention claimed is:

1. A method for the preparation of a pouch-like structure suitable for enclosing at least a part of the heart of a mammal and comprising engineered tissue, said engineered tissue comprising genetically engineered cells wherein said cells contain a gene encoding a paracrine factor and said gene being under control of an inducible promoter system or a heterologous promoter system, comprising the steps of a) providing a matrix having a recess in one surface of the matrix, said recess has appropriate dimensions to hold a defined reconstitution volume for the formation of the pouch-like structure, b) providing a body having dimensions corresponding to the desired dimensions of the interior of the pouch-like structure to be formed, and positioning the body in said recess of the matrix such that the body is spaced from the walls of said recess to form a space between the body and the walls of the recess corresponding to the reconstitution volume needed for formation of said pouch-like structure, c) positioning a reconstitution mixture in the recess, said reconstitution mixture comprising mammalian cells, and suitable scaffold material which can be incubated to form an engineered tissue structure comprising said cells, d) incubating said reconstitution mixture until the tissue construct forms within the matrix recess between the body and the matrix, e) exchanging culture medium once the pouch-like construct has formed around the body, f) removing the body with the tissue construct adherent thereto from the matrix recess, and g) separating the tissue construct from the body, wherein at least a part of said mammalian cells present in the engineered tissue structure are genetically engineered cells whereby said genetically engineered cells contain a gene encoding a paracrine factor and said gene being under control of an inducible promoter system or a heterologous promoter system.

2. The method of claim 1 wherein said genetically engineered cells are cells other than cardiac myocytes.

3. The method according to claim 1 wherein said body is an inflatable structure.

4. The method according to claim 1 wherein after step g) said engineered tissue structure is subjected to tensile stress.

5. The method according to claim 4 wherein said tensile stress is static, phasic or auxotonic stress or a combination thereof.

6. The method according to claim 1 wherein said genetically engineered cells contain a gene encoding a protein paracrine factor and/or a gene encoding RNA said gene being under control of an inducible promoter system.

7. The method according to claim 1 wherein said genetically engineered cells are cells selected from fibroblasts, smooth muscle cells endothelial cells, mesenchymal stem cells, cardiac stem cells, pericytes, leucocytes or precursor cells of said genetically engineered cells or pluripotent stem cells.

8. The method according to claim 1 wherein said inducible promoter system is a chemically inducible promoter system.

9. The method according to claim 8 wherein said chemically inducible promoter system is selected from a tetracycline based system, rapamycin based system, progesterone based system, or ecdysone based system.

10. The method according to claim 1 wherein said cells are allogenic or autologous cells of said mammal expected to receive the pouch-like structure.

11. The method of claim 6, wherein said RNA is miRNA.

12. A method for the preparation of a pouch-like structure suitable for enclosing at least a part of the heart of a mammal and comprising engineered tissue, said engineered tissue comprising genetically engineered cells wherein said cells contain a transgene encoding a paracrine factor operably linked to an inducible promoter or a heterologous promoter, wherein the genetically engineered cells are cells other than cardiac myocytes and are selected from the group consisting of fibroblasts, smooth muscle cells, endothelial cells, mesenchymal stem cells, cardiac stem cells, pericytes, leucocytes, precursor cells, and pluripotent stem cells, comprising the steps of a) providing a matrix having a recess in one surface of the matrix, said recess has appropriate dimensions to hold a defined reconstitution volume for the formation of the pouch-like structure, b) providing a body having dimensions corresponding to the desired dimensions of the interior of the pouch-like structure to be formed, and positioning the body in said recess of the matrix such that the body is spaced from the walls of said recess to form a space between the body and the walls of the recess corresponding to the reconstitution volume needed for formation of said pouch-like structure, c) positioning a reconstitution mixture in the recess, said reconstitution mixture comprising mammalian cells, and suitable scaffold material which can be incubated to form an engineered tissue structure comprising said cells, d) incubating said reconstitution mixture until the tissue construct forms within the matrix recess between the body and the matrix, e) exchanging culture medium once the pouch-like construct has formed around the body, f) removing the body with the tissue construct adherent thereto from the matrix recess, and g) separating the tissue construct from the body, wherein at least a part of said mammalian cells present in the engineered tissue structure are genetically engineered cells which contain the transgene under control of an inducible promoter system or a heterologous promoter system.

13. The method according to claim 12 wherein said engineered tissue further comprises at least one of myocytes and cells of heart tissue other than cardiac myocytes.

14. The method according to claim 12 wherein said paracrine factor has cardioprotective and/or cardio regeneration inducing activity.

15. The method according to claim 12 wherein said inducible promoter is chemically inducible.

16. The method of claim 1, wherein the mammalian cells are allogenic cells or autologous cells.

17. The method of claim 12, wherein the mammalian cells are allogenic cells or autologous cells.

* * * * *